(12) United States Patent
Dant et al.

(10) Patent No.: US 9,220,541 B1
(45) Date of Patent: Dec. 29, 2015

(54) TRANSVERSE CONNECTOR

(71) Applicant: Zimmer Spine, Inc., Minneapolis, MN (US)

(72) Inventors: Jack A. Dant, St. Paul, MN (US); Deborah L. Hoch, Minneapolis, MN (US); Eric P. Jerke, Bloomington, MN (US); Eric J. Lundequam, Hopkins, MN (US)

(73) Assignee: Zimmer Spine, Inc., Edina, MN (US)

( * ) Notice: Subject to any disclaimer, the term of this patent is extended or adjusted under 35 U.S.C. 154(b) by 0 days.

(21) Appl. No.: 14/315,722

(22) Filed: Jun. 26, 2014

(51) Int. Cl.
*A61B 17/70* (2006.01)

(52) U.S. Cl.
CPC ..... *A61B 17/7049* (2013.01); *A61B 2017/7073* (2013.01)

(58) Field of Classification Search
CPC .......... A61B 17/7002; A61B 17/7052; A61B 17/7049; A61B 17/7035; A61B 17/7037; A61B 17/704; A61B 17/7005; A61B 17/7041; A61B 17/705; A61B 17/7055; A61B 17/7032; A61B 17/7059; A61B 17/7011; A61B 17/7038; A61B 2017/7073; Y10T 24/2529; Y10T 24/2527; Y10T 403/4608; Y10T 403/4617
USPC ........... 606/246–280, 301–308; 403/396, 398
See application file for complete search history.

(56) References Cited

U.S. PATENT DOCUMENTS

| | | | |
|---|---|---|---|
| 4,488,543 A | 12/1984 | Tornier et al. | |
| 5,129,899 A | 7/1992 | Small et al. | |
| 5,234,431 A | 8/1993 | Keller | |
| 5,312,405 A | 5/1994 | Korotko et al. | |
| 5,334,203 A | 8/1994 | Wagner | |
| 5,474,551 A | 12/1995 | Finn et al. | |
| 5,487,742 A | 1/1996 | Cotrel et al. | |
| 5,601,554 A | 2/1997 | Howland et al. | |
| 5,693,053 A | 12/1997 | Estes et al. | |
| 5,997,539 A | 12/1999 | Errico et al. | |
| 6,083,226 A | 7/2000 | Fiz | |
| 6,132,430 A * | 10/2000 | Wagner | 606/264 |
| 6,171,311 B1 * | 1/2001 | Richelsoph | 606/252 |
| 6,302,883 B1 | 10/2001 | Bono | |
| 6,328,740 B1 | 12/2001 | Richelsoph | |
| 6,402,751 B1 | 6/2002 | Hoeck et al. | |
| 6,416,515 B1 | 7/2002 | Wagner | |
| 6,562,040 B1 | 5/2003 | Wagner | |
| 6,595,992 B1 | 7/2003 | Wagner et al. | |
| 6,866,664 B2 | 3/2005 | Schär | |
| 6,872,208 B1 | 3/2005 | McBride et al. | |
| 7,137,986 B2 | 11/2006 | Troxell et al. | |
| 7,578,833 B2 | 8/2009 | Bray | |
| 7,628,799 B2 | 12/2009 | Richelsoph et al. | |
| 7,699,872 B2 | 4/2010 | Farris et al. | |
| 8,241,334 B2 * | 8/2012 | Butler et al. | 606/278 |
| 9,044,272 B2 * | 6/2015 | Shaffrey et al. | 606/266 |
| 2006/0271045 A1 | 11/2006 | Hubbard et al. | |
| 2007/0123860 A1 | 5/2007 | Francis et al. | |
| 2008/0114400 A1 | 5/2008 | Dant et al. | |
| 2008/0140124 A1 | 6/2008 | Jeon et al. | |
| 2009/0018586 A1 | 1/2009 | Butler et al. | |
| 2009/0177234 A1 | 7/2009 | Butler et al. | |
| 2009/0210007 A1 * | 8/2009 | Levy et al. | 606/246 |
| 2012/0150230 A1 * | 6/2012 | Felix et al. | 606/250 |

* cited by examiner

*Primary Examiner* — Pedro Philogene
(74) *Attorney, Agent, or Firm* — Schwegman Lundberg & Woessner, P.A.

(57) ABSTRACT

A transverse connector for coupling between first and second elongate members of a spinal stabilization system. The transverse connector includes a connector arm, a first coupling assembly proximate a first end of the arm, and a second coupling assembly proximate a second end of the arm. The first and second coupling assemblies are secured to the connector arm through a plurality of mating engagement features, such as dovetail grooves.

20 Claims, 6 Drawing Sheets

TRANSVERSE CONNECTOR

TECHNICAL FIELD

The disclosure is directed to transverse connectors for use in a spinal stabilization system. More particularly, the disclosure is directed to transverse connectors which may be attached between spinal rods in a spinal stabilization system.

BACKGROUND

The spinal column is a highly complex system of bones and connective tissues that provides support for the body and protects the delicate spinal cord and nerves. The spinal column includes a series of vertebrae stacked one on top of the other. Each vertebra includes a vertebral body including an inner or central portion of relatively weak cancellous bone and an outer portion of relatively strong cortical bone. An intervertebral disc is situated between each vertebral body to cushion and dampen compressive forces experienced by the spinal column. A vertebral canal, called the foramen, containing the spinal cord and nerves is located posterior to the vertebral bodies. In spite of the complexities, the spine is a highly flexible structure, capable of a high degree of curvature and twist in nearly every direction. For example, the kinematics of the spine normally includes flexion, extension, rotation and lateral bending.

There are many types of spinal column disorders including scoliosis (abnormal curvature and twisting of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as spinal disc herniation, degenerative disc disease, fractured vertebra, and the like. Patients that suffer from such conditions usually experience extreme and debilitating pain as well as diminished range of motion and nerve function. These spinal disorders may also threaten the critical elements of the nervous system housed within the spinal column.

In some instances, a spinal stabilization system may be installed on a segment of the spinal column to stabilize a portion of the spinal column to treat a spinal disorder. One particular spinal stabilization technique includes immobilizing portions of the spine of a patient by using elongate members such as relatively rigid orthopedic spinal rods that run generally parallel to the spine on opposite sides of the spinous processes.

Installation of such systems may be accomplished, for example, by accessing the spine posteriorly and fastening hooks, bone screws, or other types of vertebral anchors to the pedicles or other bony structures of the appropriate vertebrae. The vertebral anchors may be generally placed in a quantity of two per vertebra, one on either side of the spinous processes, and serve as anchor points for the elongate members.

It may be desirable in some circumstances to provide a cross connector, such as a transverse connector, to bridge across the spinal column from a first elongate member and associated assembly of vertebral anchors to a second elongate member and associated assembly of vertebral anchors of the spinal stabilization system to provide additional stability to the spinal stabilization system. Accordingly, there exists a need to provide alternative transverse connector assemblies which may be coupled between first and second elongate members of a spinal stabilization system.

SUMMARY

The disclosure is directed to several alternative designs, materials and methods of manufacturing medical device structures and assemblies.

Accordingly, one illustrative embodiment is a transverse connector for coupling between first and second elongate members of a spinal stabilization system. The transverse connector may comprise a connector arm having a first end portion, a second end portion and a bridge member extending therebetween. The first end portion may have a first through hole extending from a top surface to a bottom surface thereof and the second end portion may have a second through hole extending from a top surface to a bottom surface thereof. The connector arm may further include a first upper pair of dovetail grooves extending along the top surface adjacent to the first through hole, a first lower pair of dovetail grooves extending along the bottom surface adjacent to the first through hole, a second upper pair of dovetail grooves extending along the top surface adjacent to the second through hole, and a second lower pair of dovetail grooves extending along the bottom surface adjacent to the second through hole. A first coupling assembly may be positioned proximate the first end portion of the connector arm. The first coupling assembly may comprise a first sleeve having a top surface, a bottom surface, an aperture extending between the top surface and the bottom surface, and a pair of dovetail grooves extending along the top surface. The first coupling assembly may further include a first insert having a first end region and a second end region and a first locking mechanism having a dovetail groove extending around a perimeter of a lower portion thereof. The transverse connector may further include a second coupling assembly positioned proximate to the second end portion of the connector arm. The second coupling assembly may comprise a second sleeve having a top surface, a bottom surface, an aperture extending between the top surface and the bottom surface, and a pair of dovetail grooves extending along the top surface. The second coupling assembly may further include a second insert having a first end region and a second end region and a second locking mechanism having a dovetail groove extending around a perimeter of a lower portion thereof.

Another illustrative embodiment is a transverse connector for coupling between first and second elongate members of a spinal stabilization system. The transverse connector may comprise a connector arm having a first end portion, a second end portion and a bridge member extending therebetween along a longitudinal axis. The first end portion may have a first through hole extending from a top surface to a bottom surface thereof and the second end portion may have a second through hole extending from a top surface to a bottom surface thereof. The connector arm may further include a first upper pair of dovetail grooves extending along the top surface adjacent to the first through hole, a first lower pair of dovetail grooves extending along the bottom surface adjacent to the first through hole, a second upper pair of dovetail grooves extending along the top surface adjacent to the second through hole, and a second lower pair of dovetail grooves extending along the bottom surface adjacent to the second through hole. A first coupling assembly may be positioned proximate to the first end portion of the connector arm. The first coupling assembly may comprise a first sleeve having a top surface, a bottom surface, an aperture extending between the top surface and the bottom surface, and a pair of dovetail grooves extending along the top surface and configured to slidably engage the first pair of lower dovetail grooves of the connector arm in a direction generally parallel to the longitudinal axis of the connector arm. The first coupling assembly may further comprise a first insert having a first end region and a second end region, the first insert being movably disposed within the aperture of the first sleeve and a first locking mechanism having a dovetail groove extending around a perimeter of a lower portion thereof and configured to slidably engage the first pair of upper dovetail grooves of the connector arm in a direction generally parallel to the longitudinal axis of the connector arm. The transverse connector may further include a second coupling assembly proximate the second end portion of the connector arm. The second coupling assembly may comprise a second sleeve having a top surface, a bottom surface, an aperture extending between the top surface and the bottom surface, and a pair of dovetail grooves extending along the top surface and configured to slidably engage the second pair of lower dovetail grooves of the connector arm in a direction generally parallel to the longitudinal axis of the connector arm. The second coupling assembly may further comprise a second insert having a first end region and a second end region, the second insert being movably disposed within the aperture of the second sleeve and a second locking mechanism having a dovetail groove extending around a perimeter of a lower portion thereof and configured to engage the second pair of upper dovetail grooves of the connector arm in a direction generally parallel to the longitudinal axis of the connector arm.

Another illustrative embodiment is a spinal stabilization system. The spinal stabilization system may comprise a first and a second elongate member. A transverse connector may extend between the first elongate member and the second elongate member. The transverse connector may comprise a connector arm having a first end portion, a second end portion and a bridge member extending therebetween, the first end portion having a first through hole extending from a top surface to a bottom surface and the second end portion having a second through hole extending from a top surface to a bottom surface. The connector arm may further include a first upper pair of dovetail grooves extending along the top surface adjacent to the first through hole, a first lower pair of dovetail grooves extending along the bottom surface adjacent to the first through hole, a second upper pair of dovetail grooves extending along the top surface adjacent to the second through hole, and a second lower pair of dovetail grooves extending along the bottom surface adjacent to the second through hole. The transverse connector may further include a first coupling assembly proximate the first end portion of the connector arm. The first coupling assembly may comprise a first sleeve having a top surface, a bottom surface, an aperture extending between the top surface and the bottom surface, and a pair of dovetail grooves extending along the top surface. The first coupling assembly may further comprise a first insert having a first end region and a second end region and a first locking mechanism having a dovetail groove extending around a perimeter of a lower portion thereof. The transverse connector may further include a second coupling assembly proximate the second end portion of the connector arm. The second coupling assembly may comprise a second sleeve having a top surface, a bottom surface, an aperture extending between the top surface and the bottom surface, and a pair of dovetail grooves extending along the top surface. The second coupling assembly may further include a second insert having a first end region and a second end region and a second locking mechanism having a dovetail groove extending around a perimeter of a lower portion thereof.

The above summary of some example embodiments is not intended to describe each disclosed embodiment or every implementation of the invention.

BRIEF DESCRIPTION OF THE DRAWINGS

The disclosure may be more completely understood in consideration of the following detailed description of various embodiments in connection with the accompanying drawings, in which.

Figure 1:
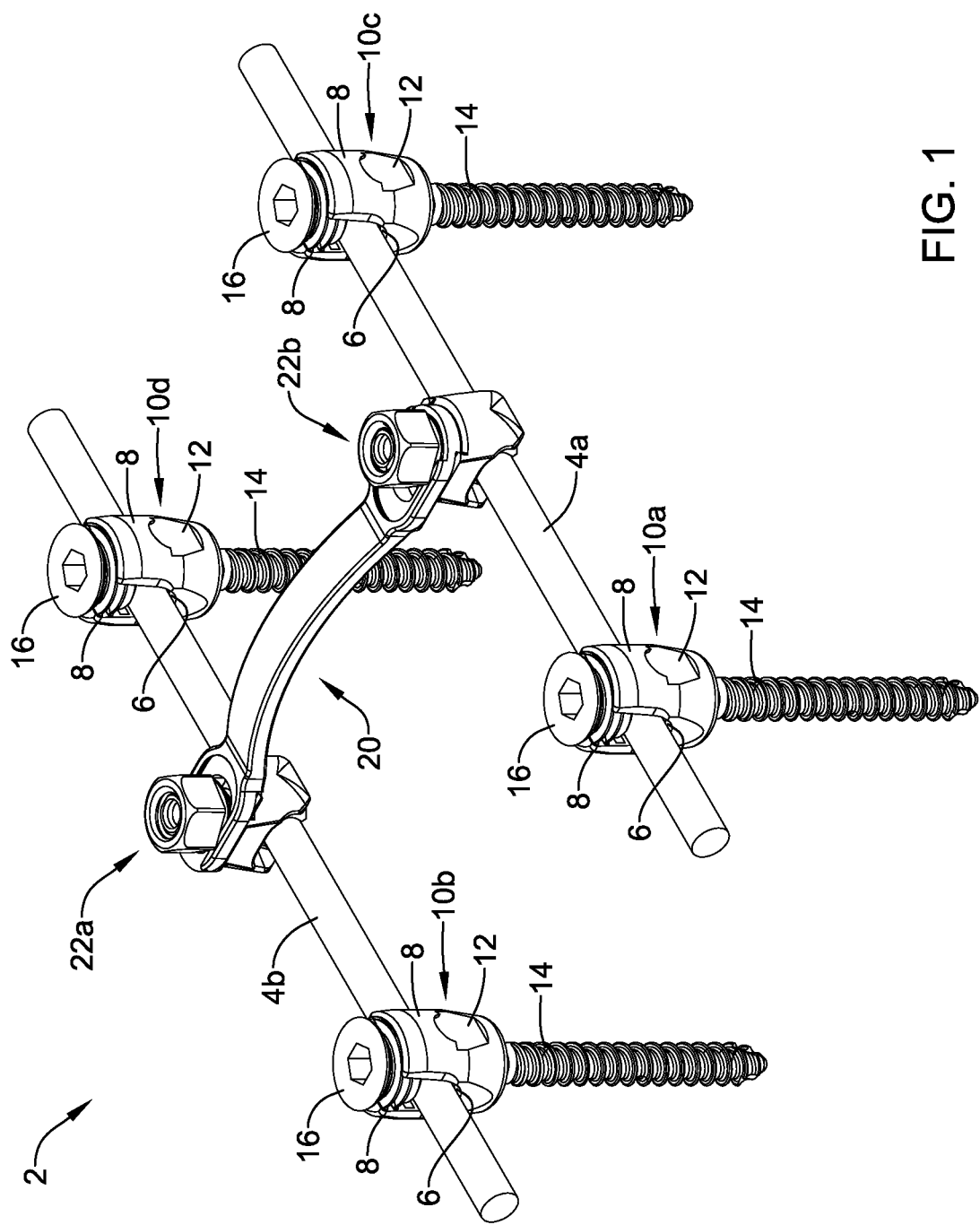
FIG. 1 is a perspective view of an exemplary spinal stabilization system including a transverse connector extending between elongate members.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure. The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Now referring to the drawings, an exemplary spinal stabilization system 2 for stabilizing a portion of a spinal column, such as one or more spinal segments of a spinal column, is illustrated in FIG. 1. As used herein, a spinal segment is intended to refer to two or more vertebrae, the intervertebral disc(s) between the vertebrae and other anatomical elements between the vertebrae. For example, a spinal segment may include first and second adjacent vertebrae and the intervertebral disc located between the first and second vertebrae. The spinal stabilization system 2 may provide support to the spinal segment subsequent bone fusion, may help preserve the facet joints between adjacent vertebrae by providing facet offloading and/or may stabilize or reverse neural foraminal narrowing of the spinal column, in some instances.

In some embodiments, the spinal stabilization system 2 may be used to treat discogenic low back pain, degenerative spinal stenosis, disc herniations, facet syndrome, posterior element instability, adjacent level syndrome associated with spinal fusion, and/or other maladies associated with the spinal column.

The spinal stabilization system 2 may include one or more or a plurality of vertebral anchors 10 and elongate members 4 extending therebetween. Although the vertebral anchors 10 are depicted as threaded vertebral fasteners (e.g., pedicle screws, bone screws), in some embodiments the vertebral anchors 10 may be vertebral hooks (e.g., laminar hooks) or other types of fastening members for attachment to a bony structure such as a vertebra of the spinal column. Each of the vertebral anchors 10 may be configured to be secured to a vertebra of a spinal column.

The spinal stabilization system 2 may be used in any desired region of the spinal column, such as the cervical, thoracic, thoracolumbar, and lumbar regions. The vertebral stabilization system 2 may be installed multi-laterally on opposite sides of the sagittal plane of the spinal column, with the first and third vertebral anchors 10a, 10c and the first elongate member 4a positioned on one lateral side of the sagittal plane and the second and fourth vertebral anchors 10b, 10d and the second elongate member 4b positioned on the other lateral side (i.e., contra-lateral side) of the sagittal plane. For instance, the first vertebral anchor 10a and the second vertebral anchor 10b may be secured to a first vertebra on contra-lateral sides of the sagittal plane, while the third vertebral anchor 10c and the fourth vertebral anchor 10d may be secured to a second vertebra on contra-lateral sides of the sagittal plane. Additional vertebral anchors 10 may be secured to additional vertebrae as desired.

The vertebral anchor 10 may include a housing 12 and a bone engagement portion, such as a bone screw 14 extending from the housing 12 along a longitudinal axis of the vertebral anchor 10. In some embodiments, the vertebral anchor 10 may be a monoaxial screw in which the housing 12 is stationary relative to the bone screw 14, while in other embodiments the vertebral anchor 10 may be a polyaxial screw in which the housing 12 is actuatable (e.g., pivotable) relative to the bone screw 14. In yet other embodiments, the vertebral anchor may be a monoaxial screw, a uniplanar screw, a bone hook, or the like. In some embodiments, the bone screw 14 may be configured to be installed into a bony region of a vertebra of the spinal column. For example, the bone screw 14 may be installed into a pedicle of a vertebra, or other region of a vertebra. In some embodiments, the bone screw 14 may include helical threads configured to be screwed into a pedicle of a vertebra, or other bony region of a vertebra.

The housing 12 may include a base portion and first and second legs 8 extending from the base portion and defining a channel 6, such as a U-shaped channel, therebetween extending into the housing 12 from an upper extent of the housing 12 opposite the bone screw 14. In some embodiments each of the first and second legs 8 may include a threaded portion for threadedly engaging a threaded portion of a fastener 16. In other embodiments, the first and second legs 8 may include other engagement features for engaging with a securing member positioned in the housing 12 between the first and second legs 8.

The spinal stabilization system 2 may also include one or more, or a plurality of elongate stabilization members 4a, 4b (collectively 4), such as elongate rods, extending between vertebral anchors 10 of the spinal stabilization system 2. As an illustrative example, the spinal stabilization system 2 shown in FIG. 1 includes a first elongate member 4a extending between and secured to the first vertebral anchor 10a and the third vertebral anchor 10c, and a second elongate member 4b extending between and secured to the second vertebral anchor 10b and the fourth vertebral anchor 10d.

The elongate members 4 may be secured in the channels 6 of the housings 12 of the vertebral anchors 10 using threaded fasteners or other securement members. For instance, threaded set screws 16 may be threadably engaged with the threaded portions of the legs 8 of the housings 12 of the vertebral anchors 10 and press against the elongate member 4 to secure the elongate members 4 in the channels 6.

The spinal stabilization system 2 may also include a transverse connector 20 which may be positioned generally perpendicular to the elongate members 4 to provide additional stability to the spinal stabilization system 2 in some instances. The transverse connector 20 may be configured to be coupled to the elongate stabilization members 4. For example, the transverse connector 20 may be coupled between the first and second stabilization members 4a, 4b in an orientation generally perpendicular to the elongate members 4. Opposing ends of the transverse connector 20 may include coupling assemblies 22, each configured to engage an elongate member 4.

While the transverse connector 20 is illustrated as being positioned between contralateral spinal rods on either lateral side of sagittal plane at a single spinal level, it is contemplated that the transverse connector 20 may be configured to allow for multilevel connection in some instances. In other words, in some instances, the first coupling assembly 22a may be coupled to a first elongate member 4 between a first vertebra and a second vertebra on a first lateral side of the sagittal plane, and the second coupling assembly 22b may be coupled to a second elongate member 4 between the second vertebra and a third vertebra on a second lateral side of the sagittal plane opposite the first lateral side. For example, in some instances, a first coupling assembly 22a may be positioned between the C3 and C4 vertebrae and a second coupling assembly 22b may be positioned between the C4 and C5 vertebrae. In such an instance, the transverse connector 20 may be positioned at an oblique angle to the elongate members 4. This is just an example; it is contemplated that the first and second coupling assemblies 22a, 22b may be positioned between any vertebrae desired.

It is further contemplated that the transverse connector 20 may be configured to attach to the housing 12 of one or more of the vertebral anchors 10 in some instances. For example, the insert 38 of the coupling assembly 22 may be configured to clamp onto the housing 12 of a vertebral anchor 10, or other structural component of a vertebral anchor 10, if desired.

Figure 2:
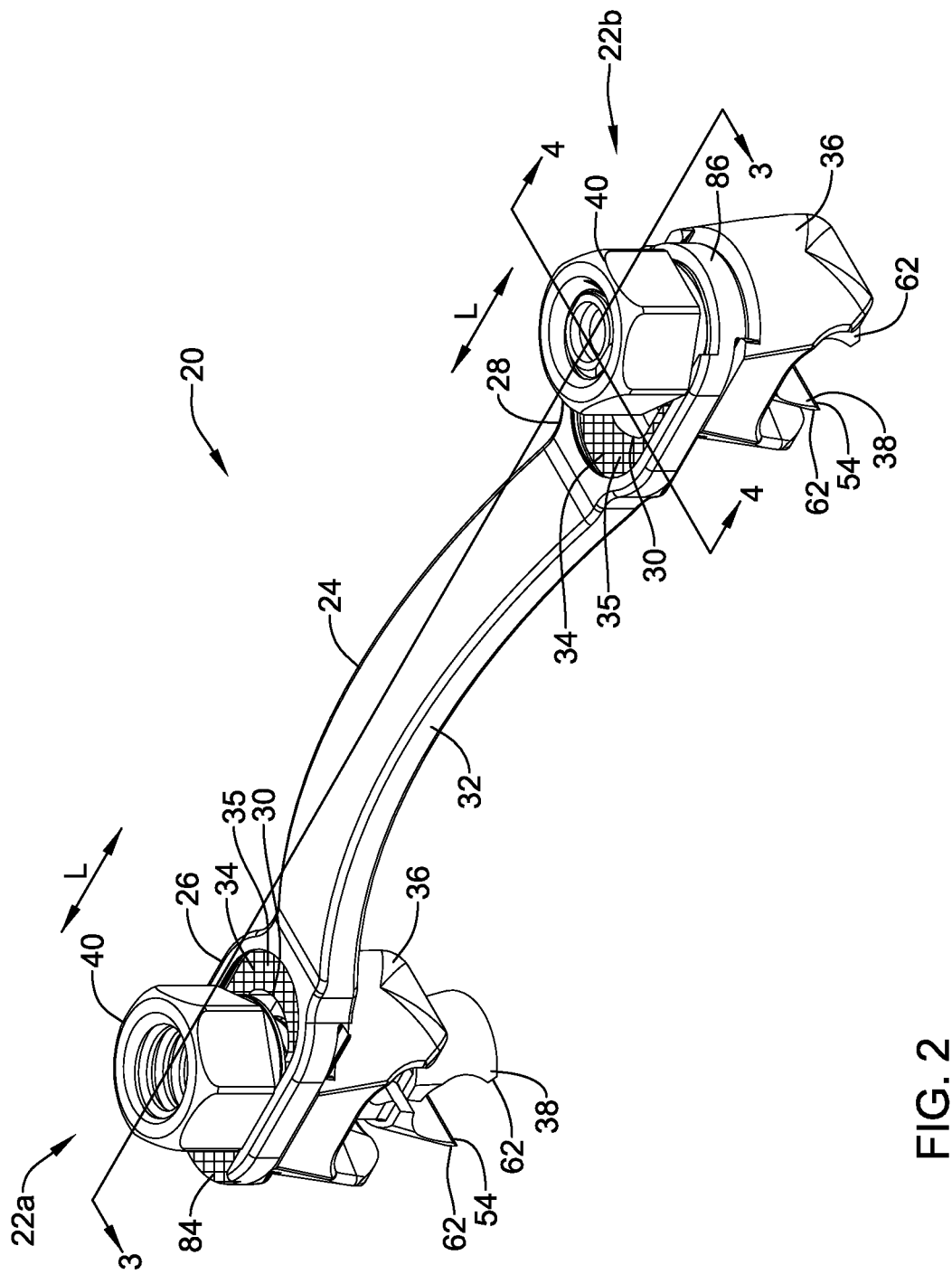
FIG. 2 is a perspective view of the transverse connector shown in FIG. 1.

Additional features and components of the transverse connector 20 are further illustrated in FIGS. 2-6. As shown in FIG. 2, which illustrates a perspective view of the transverse connector 20, the transverse connector 20 may include a connector arm 24 having a first end portion 26, a second end portion 28, and a bridge member 32 extending between the first end portion 26 and the second end portion 28. The bridge member 32 may have an arcuate or curved shape, although this is not required. The first and second end portions 26, 28 may each include a through hole 30 extending therethrough. In some instances, the through holes 30 may have a generally oblong or elongated shape, although this is not required. It is contemplated that the through holes 30 may take any shape desired, such as, but not limited to, round, square, rectangular, polygonal, etc. In some instances, the through holes 30 may be sized to allow for some longitudinal movement of coupling assemblies 22 in direction L such that the transverse connector 20 can be adapted to the varying anatomies of different patients. An upper surface 34 and a lower surface (not explicitly shown) may surround a perimeter of each of the through holes 30. In some instances, the upper surface 34 and the lower surface may be a textured surface 35 to help secure the coupling assemblies 22. In some embodiments, the textured surface 35 may be grooved, ridged, bumped, etc., to increase the surface area of the surface and/or to increase the friction between the connector arm 24 and the coupling assemblies 22.

Figure 3:
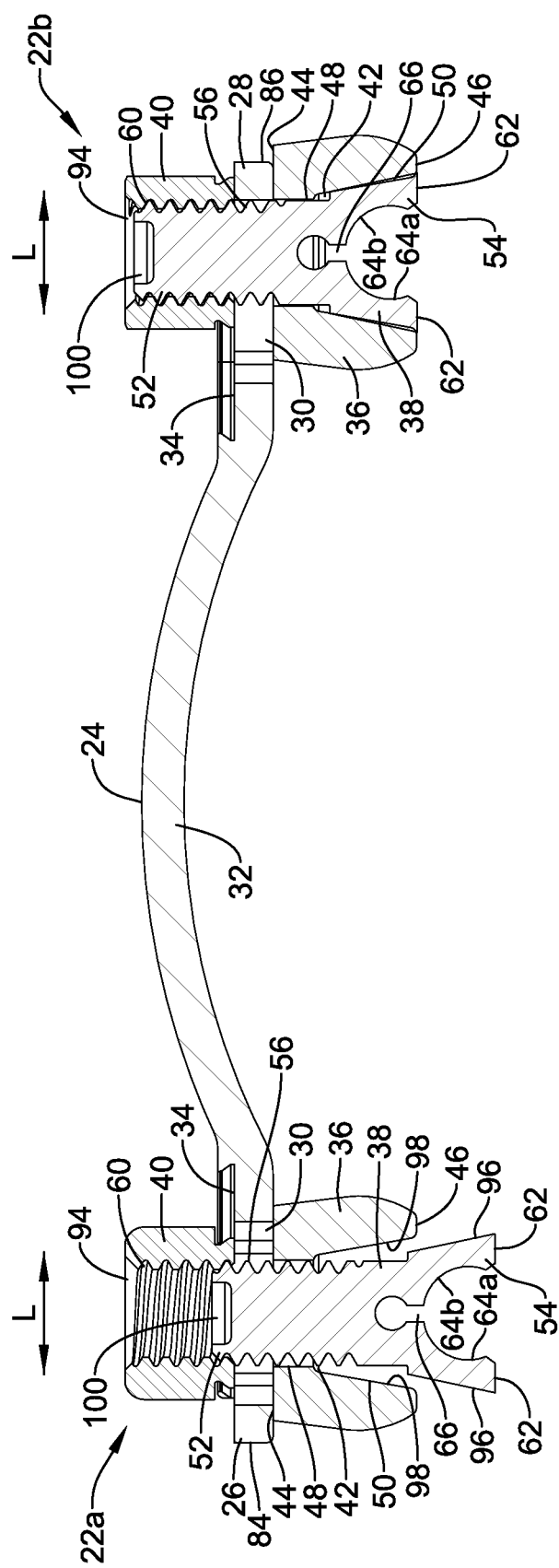
FIG. 3 is a cross-sectional view of the transverse connector of FIG. 2 taken along line 3-3 of FIG. 2.

Referring additionally to FIG. 3, which illustrates a cross-sectional view of transverse connector 20 taken at line 3-3 of FIG. 2, the transverse connector 20 may include a first coupling assembly 22a and a second coupling assembly 22b secured to the connector arm 24 at each of the through holes 30. The first coupling assembly 22a is shown in a first configuration and the second coupling assembly 22b is shown in a second configuration, as will be described in more detail below. It is noted that although the coupling assemblies 22a, 22b are shown in two different configurations, the coupling assemblies 22 may be similarly configured and include similar components.

Each coupling assembly 22 may include multiple components, including an insert 38, a sleeve 36, and a locking mechanism 40 cooperating to secure connector arm 24 between two elongate members 4. It is noted that although one coupling assembly 22 at one end of the transverse connector 20 is described herein, the coupling assembly 22 at the other end of the transverse connector 20 may be similarly configured and include similar components. The sleeve 36 may include a central aperture 42 extending from a top surface 44 to a bottom surface 46 of the sleeve 36. The aperture 42 may have a first end region 48 having a generally constant cross-sectional shape adjacent to the top surface 44. The aperture 42 may have a second end region 50 which tapers from a first cross-section shape adjacent to the bottom surface 46 towards a second, smaller cross-sectional shape adjacent to the first end region 48. In some instances, the second end region 50 may, in part, have a generally conical tapered surface shaped to contact an outer surface of the insert 38, as will be discussed in more detail below. It is contemplated that the second end region 50 may slope at an angle of approximately 20°, approximately 25°, or approximately 30°, although this is not required. It is contemplated that the slope may be any oblique angle to the longitudinal axis of the aperture 42 desired.

The insert 38 may be slidably disposed within the aperture 42 of the sleeve 36 and the through hole 30 of the connector arm 24. For example, the insert 38 may move up and down within the aperture 42 of the sleeve 36 along the longitudinal rotational axis of the insert 38, as will be discussed in more detail below. Furthermore, the insert 38 may slide together with the sleeve 36 along the direction L of FIG. 2. The insert 38 may include a first end region 52 and a second end region 54. The first end region 52 may include a threaded portion 56, such as an externally threaded post portion, configured to engage a threaded portion 60, such as an internally threaded bore, of the locking mechanism 40 and flat regions 58 (see FIGS. 4 and 5). The flat regions 58 may allow for some rotation, for example ±10° from the longitudinal axis of the transverse connector 20, yet prevent the insert 38 from fully rotating 360° within the through hole 30. The aperture 42 of the sleeve 36 may also include features to limit the rotation of the insert 38, as will be discussed in more detail below. The ability of the insert 38 to rotate through a limited amount of rotation, such as an angle less than 360°, less than 180°, less than 90°, less than 45°, or less than 30° may allow the transverse connector 20 to extend between two elongate members 4 that are not parallel. The distance across the insert 38 between the flat regions 58 and perpendicular to the longitudinal axis of the insert 38 may be less than the width of the through hole 30 of the connector arm 24 and the portion of the aperture 42 of the sleeve 36 through which the threaded portion 56 extends, while the transverse distance across the insert 38 between the discontinuous threaded portions between the flat region 58 and perpendicular to the longitudinal axis of the insert 38 may be greater than the width of the through hole 30 such that the insert 38 may be positioned through the through hole 30, while restricting rotation movement of the insert 38 in the hole 30.

The first end region 52 may extend through the aperture 42 of the sleeve 36 and through hole 30 in the connector arm 24. The locking mechanism 40 may threadably engage insert 38 to secure the insert 38 to the connector arm 24. For instance, the threaded portion of the locking mechanism 40 may threadably mate with the threaded portion of the insert 38. In some instances, the locking mechanism 40 may be a nut, although this is not required. A divot 100 may be formed adjacent to the threaded portion 56.

The second end region 54 of the insert 38 may include a pair of angled arms 54 each having an arcuate or curved inner surface 64a, 64b (collectively 64). The curved inner surfaces 64 may be sized and shaped to generally conform to or grasp an outer surface of elongate member 4. In some instances, the center of radius of the radius cuts forming the curved inner surfaces 64a, 64b may not be co-located. For example, the center of radius of the radius cut of the first curved inner surface 64a may be offset from the longitudinal axis of the insert in a first direction and the center of radius of the radius cut of the second curved inner surface 64b may be offset from the longitudinal axis of the insert 38 in a second direction generally opposite from the first direction. Offsetting the centers of radii of the curved inner surfaces 64a, 64b may reduce or minimize the amount of force required to snap the insert 38 onto the elongate member 4. It is contemplated that when the arms 62 are compressed by the sleeve 36, as discussed in more detail below, the arms 62 are moved inward towards one another such that the center of radii of the radius cuts are generally aligned along the same central axis of the elongate member 4.

The insert 38 may further include an opening or gap 66 between the arms 62 to allow the arms 62 to flex inwards towards one another, as will be described in more detail below. The opening between the arms 54 may be sized to be slightly less than the diameter of the elongate member 4 positionable therein, such that the insert 38 snaps onto the elongate member 4 and surrounds more than 180° of the elongate member 4 to provisionally couple the insert 38 to the elongate member 4 prior to locking the transverse connector 20 to the elongate member 4 with the locking mechanism 40.

Figure 4:
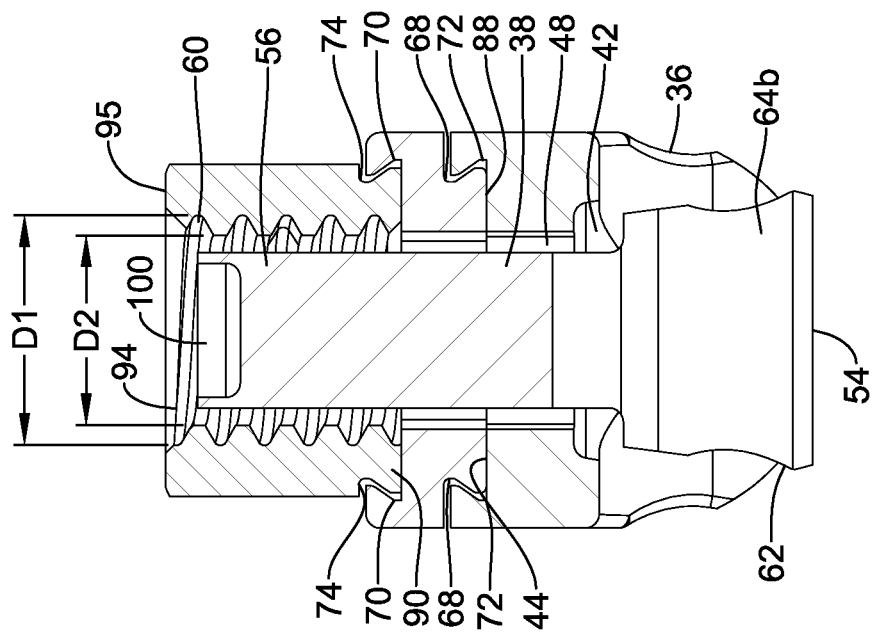
FIG. 4 is a cross-sectional view of a coupling portion of the transverse connector of FIG. 2 taken along line 4-4 of FIG. 2.
Figure 5:
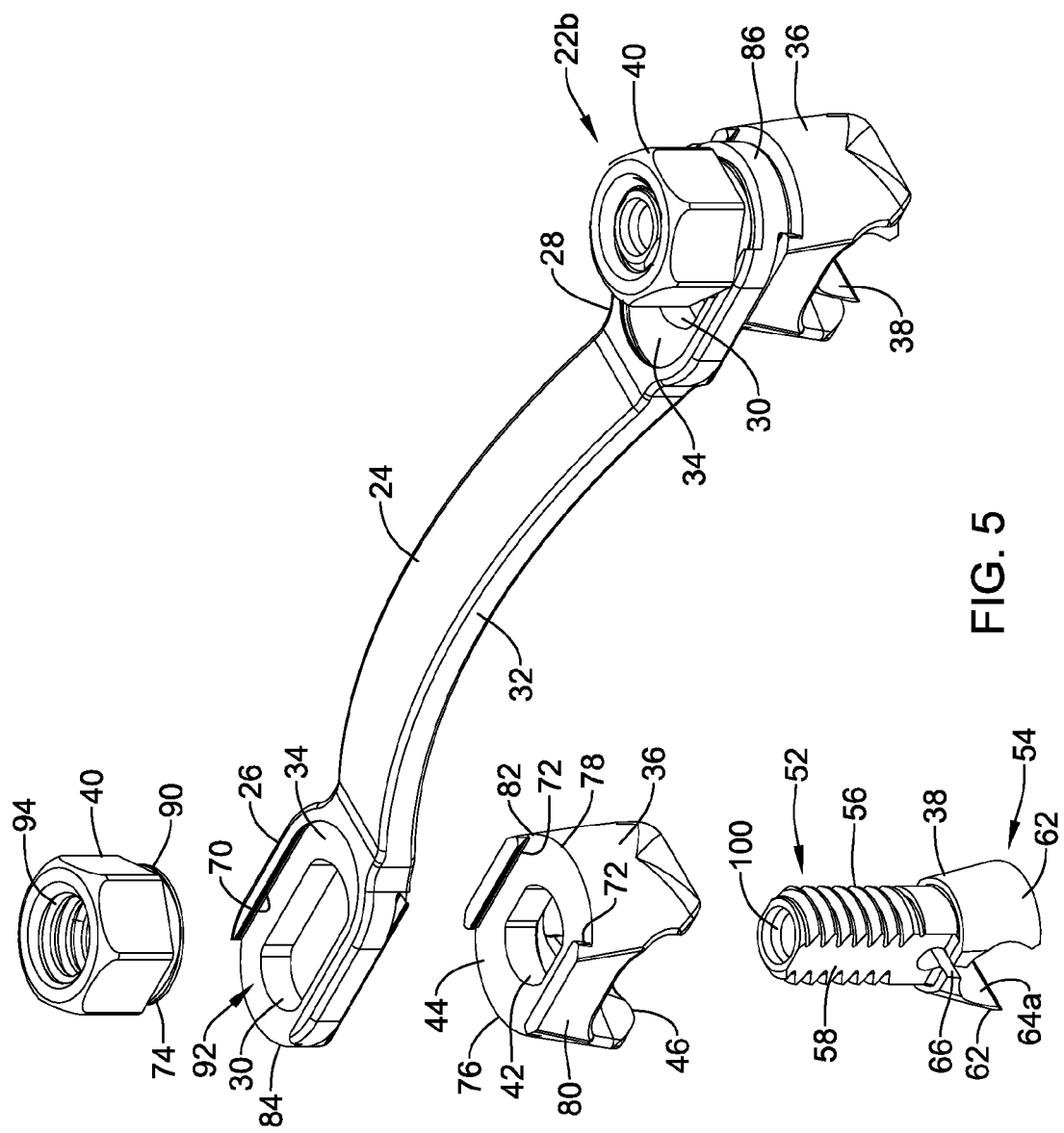
FIG. 5 is an exploded perspective view of components of a coupling portion of the transverse connector of FIG. 2.
Figure 6:
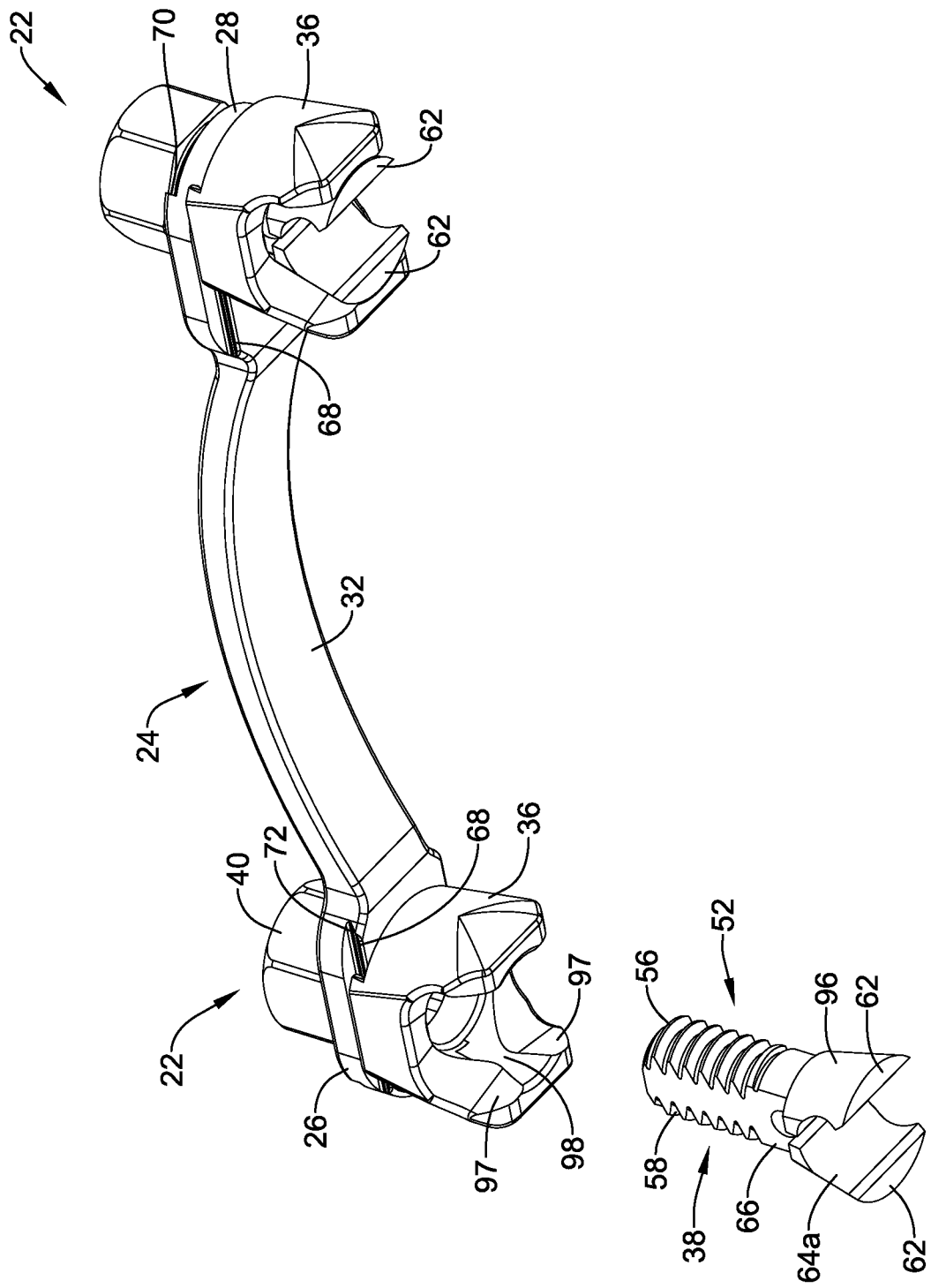
FIG. 6 is another perspective view of components of a coupling portion of the transverse connector of FIG. 2.

Referring to FIG. 4, which illustrates a cross-sectional view of transverse connector 20 taken at line 4-4 of FIG. 2, and FIG. 5, which illustrates a perspective view of a partially exploded transverse connector 20, the locking mechanism 40 and sleeve 36 may be releasably connected to the connector arm 24 through a series of mating engagement or retention elements, such as, but not limited to dovetail features (e.g., mating dovetail flanges and/or grooves). While the engagement elements or members are described as dovetail grooves, it is contemplated that the locking mechanism 40, sleeve 36, and connector arm 24 may include a variety of structural features configured to releasably secure the locking mechanism 40 and sleeve 36 to the connector arm 24. These structural features include but are not limited to mating dovetail grooves, a tongue and groove structure, flanges and corresponding grooves, pins or other protruding elements, etc.

The lower surface of the connector arm 24 may include an engagement feature, for example, a pair of lower grooves, such as dovetail grooves 68, and/or the upper surface of the connector arm 24 may include an engagement feature, for example, and a pair of upper grooves, such as dovetail grooves 70. The engagement features (e.g., dovetail grooves 68, 70) may extend generally parallel to a longitudinal axis of the connector arm 24 on either side of the through hole 30. The sleeve 36, which may be positioned below the connector arm 24, may include an engagement feature, for example, a pair of flanges and/or grooves, such as dovetail grooves or flanges 72 positioned adjacent to the top surface 34 thereof configured to mate with the engagement feature (e.g., dovetail grooves 68) on the lower surface of the connector arm 24. The engagement features (e.g., dovetail grooves 72) may extend along the top surface 44 from a first end 76 to a second end 78 and adjacent to a first side 80 and a second side 82 (see FIG. 5) of the sleeve 36. The lower engagement feature (e.g., dovetail grooves 68) may have an open region (not explicitly shown) near the first end 84 (or second end 86) of the connector arm 24 such that the engagement feature (e.g., dovetail grooves 72) on the sleeve 36 may be slidably engaged with the engagement feature (e.g., dovetail grooves 68) on the lower surface of the connector arm 24. It is contemplated that when the engagement features (e.g., dovetail grooves 68, 72) are engaged with one another, the sleeve 36 may be held in a position adjacent to the lower surface 88 of the connector arm 24, as shown in FIG. 4.

The locking mechanism 40, which may be positioned above the connector arm 24, may include an engagement feature, for example, a flange, such as a dovetail groove or flange 74 extending around a circumference of the lower portion 90 thereof. The upper engagement feature (e.g., dovetail grooves 70) of the connector arm 24 may have an open region 92 near the first end 84 (or second end 86) of the connector arm 24 such that the engagement feature or flange (e.g., dovetail groove 74) on the locking mechanism 40 may be slidably engaged with the engagement feature (e.g., dovetail grooves 70) on the upper surface of the connector arm 24. The circumferential flange (e.g., dovetail groove 74) may allow the locking mechanism 40 to rotate relative to the connector arm 24, the sleeve 36 and/or the insert 38 while releasably securing the locking mechanism 40 to the connector arm 24 via mating engagement features (e.g., dovetail grooves 70, 74).

To assemble the transverse connector 20, the sleeve 36 may be slid onto the connector arm 24 in a direction generally parallel to the longitudinal axis of the transverse connector 20 with the engagement feature (e.g., flanges, grooves, dovetail grooves 72) of the sleeve 36 mating with the lower engagement feature (e.g., flanges, grooves, dovetail grooves 68) of the connector arm 24. The locking mechanism 40 may be slid onto the connector arm 24 in a direction generally parallel to the longitudinal axis of the transverse connector 20 with the engagement feature (e.g., flange, groove, dovetail groove 74) of the locking mechanism 40 mating with the upper engagement feature (e.g., flanges, grooves, dovetail grooves 70) of the connector arm 24. The sleeve 36 and the locking mechanism 40 may be vertically aligned such that the aperture 42 in the sleeve 36 generally aligns with a through hole 94 (e.g., threaded bore) in the locking mechanism 40. The first end region 52 (e.g., threaded post) of the insert 38 may then be inserted upwards through the aperture 42 in the sleeve 36 until it begins to engage the locking mechanism 40, as shown in connector assembly 22a in FIG. 3. The locking mechanism 40 may then be rotated to threadably engage the locking mechanism 40 with the insert 38. Rotating in a first direction, such as clockwise, or tightening the locking mechanism 40 may raise the second end region 54 of the insert 38 into the aperture 42 of the sleeve 36, as shown in connector assembly 22b in FIG. 3. As the insert 38 is drawn into the aperture 42 of sleeve 36, an outer surface 96 of the arms 62 may contact an inner surface 98 (see FIG. 6) of the sleeve 36. The inner surface 98 may have a generally conical tapered surface shaped to contact the outer surface 96 of the insert 38. It is contemplated that the inner surface 98 may slope at an angle of approximately 20°, for example, although this is not required. It is contemplated that the slope may be any oblique angle to the longitudinal axis of the insert 38 desired. The inner surface 98 of the sleeve 36 may be sized and shaped such that the arms 62 of the insert 38 form a point and/or line contact with the inner surface 98. It is further contemplated that the second end region 50 of aperture 42 may be slightly smaller than the outer profile of the arms 62 of the insert 38. This may cause the arms 62 to compress towards one another when the arms 62 are disposed within the sleeve 36, allowing the insert 38 to grasp the elongate member 4 positioned therebetween. Rotating the locking mechanism 40 in a second direction opposite the first direction, such as counter-clockwise, or loosening the locking mechanism 40, may cause the insert 38 to lower out of the housing 36. The mating engagement features (e.g., flanges, grooves, dovetail grooves 68, 72) of the connector arm 24 and the sleeve 36 may allow the insert 38 to be raised and lowered while maintaining the sleeve 36 in a desired position. For example, the mating engagement features (e.g., flanges, grooves, dovetail grooves 68, 72) of the connector arm 24 and the sleeve 36 may hold the sleeve 36 up and juxtaposed with the lower surface of the connector arm 24 while the insert 38 is lowered to engage the elongate member 4. When the surfaces 96 of the insert 38 is lowered away from the inner surface 98 of the sleeve 36, the arms 62 of the insert 38 may be slayed or deflected outward to permit the elongate member 4 to be inserted into the opening between the arms 62.

In some embodiments, the channel extending through the sleeve 36 for accommodating the elongate member 4 therethrough may include one or more recesses 97 opening out on opposing sides of the sleeve 36. The recesses 97 may be positioned adjacent to a central inner conical surface 98. The recesses 97 permit the elongate member 4 to extend at a non-perpendicular angle to the transverse connector 20, and therefore allow for increased angulation of the elongate member 4 relative to the longitudinal axis of the transverse connector 20. For example, the recesses 97 may allow the transverse connector 20 to extend between two elongate members 4 without being perpendicular to one or more of the elongate members 4. For example, the transverse connector 20 may extend at an oblique angle to one or more of the elongate members 4, such as at an angle between about 30° to 90°, between about 45° to 90°, or between about 60° to 90° from the elongate member 4. Thus the transverse connector 20, including the sleeve 36, may be rotated relative to the insert 38 about the longitudinal axis of the insert 38 with the insert 38 clipped onto the elongate member 4 before final tightening of the locking mechanism 40 to secure the transverse connector 20 to the elongate member 4.

It is contemplated that the transverse connector 20 may be shipped to the customer in its assembled state. To couple the transverse connector 20 between two elongate members 4, the physician may rotate the locking mechanism 40 to lower the insert 38 out of the sleeve 36 as shown in coupling assembly 22a in FIGS. 2 and 3, if so needed. In some instances, the transverse connector 20 may be provided with the insert 38 lowered out of the sleeve 36 as shown in coupling assembly 22a in FIGS. 2 and 3. The arms 62 of the insert 38 may be deflected around the elongate members 4 to couple the elongate members 4 thereto. The locking mechanism 40 may then be rotated to raise the insert 38 into the sleeve 36 and thereby draw the surfaces 96 of the arms 62 of the insert 38 into contact with the inner surface 98 of the sleeve 36 as shown in coupling assembly 22b in FIGS. 2 and 3. As discussed above, the inner surface 98 of the sleeve 36 may apply a compressive force on the outer surface 96 of the arms 62 to further secure the elongate member 4 between the arms 62.

In some instances, the threaded region 60 of the locking mechanism 40 may have a major diameter D1 and a minor diameter D2 (see FIG. 4). The major diameter D1 may remain constant over the length of the threaded region 60. In some embodiments, the minor diameter D2 may taper from a first diameter proximate an upper end 95 of the threaded region 60 to a second smaller diameter adjacent to the lower portion 90, although this is not required. It is contemplated that the minor diameter D2 may change in a step-wise manner over the length of the threaded region 60, or gradually, for example. In some instances, there may be two or more different minor diameters D2 over the length of the threaded region 60. In some instances, the minor diameter D2 may remain constant over the length of the threaded region 60.

It is contemplated that subsequent to threading the threaded region 56 of the insert 38 into the threaded region 60 of the locking member 40 from the lower portion 90 toward the upper end 95 of the locking mechanism 40, the upper end of the threaded portion 56 of the insert 38 may be flared outward sufficiently to prevent the flared upper portion from coming unthreaded from the locking mechanism 40. For example, the threading of the flared upper portion of the insert 38 may have a major diameter less than the major diameter D1 of the threaded region 60, while the minor diameter of the flared upper portion of the insert 38 may be less than the minor diameter D2 proximate the upper end 95 of the threaded region 60 yet greater than the minor diameter D2 proximate the lower portion 90 of the threaded region 60. Accordingly, the flared upper portion of the insert 38 may hang up on the smaller minor diameter D2 proximate the lower portion 90 of the locking mechanism 40 to couple the insert 38 and locking mechanism 40 together, and thus prevent the two components from being decoupled.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A transverse connector for coupling between first and second elongate members of a spinal stabilization system, the transverse connector comprising:
   a connector arm having a first end portion, a second end portion and a bridge member extending therebetween, the first end portion having a first through hole extending from a top surface to a bottom surface and the second end portion having a second through hole extending from a top surface to a bottom surface, wherein the connector arm further includes a first upper pair of dovetail grooves extending along the top surface adjacent to the first through hole, a first lower pair of dovetail grooves extending along the bottom surface adjacent to the first through hole, a second upper pair of dovetail grooves extending along the top surface adjacent to the second through hole, and a second bottom pair of dovetail grooves extending along the lower surface adjacent to the second through hole;
   a first coupling assembly proximate the first end portion of the connector arm, the first coupling assembly comprising:
      a first sleeve having a top surface, a bottom surface, an aperture extending between the top surface and the bottom surface, and a pair of dovetail grooves extending along the top surface configured to slidably engage the first lower pair of dovetail grooves of the connector arm;
      a first insert extending through the first through hole, the first insert having a first end region and a second end region; and
      a first locking mechanism coupled to the first insert and having a dovetail groove extending around a perimeter of a lower portion thereof configured to slidably engage the first upper pair of dovetail grooves of the connector arm;
   a second coupling assembly proximate the second end portion of the connector arm, the second coupling assembly comprising:
      a second sleeve having a top surface, a bottom surface, an aperture extending between the top surface and the bottom surface, and a pair of dovetail grooves extending along the top surface configured to slidably engage the second lower pair of dovetail grooves of the connector arm;
      a second insert extending through the second through hole, the second insert having a first end region and a second end region; and
      a second locking mechanism coupled to the second insert and having a dovetail groove extending around a perimeter of a lower portion thereof configured to slidably engage the second upper pair of dovetail grooves of the connector arm.

2. The transverse connector of claim 1, wherein the first insert is rotatable in the first through hole through an angle of less than 360° and the second insert is rotatable in the second through hole through an angle of less than 360°.

3. The transverse connector of claim 1, wherein the connector arm has a longitudinal axis and the first sleeve and the first locking mechanism are configured to slidingly engage the first lower pair of dovetail grooves and the first upper pair of dovetail grooves, respectively, of the connector arm in a first direction generally parallel to the longitudinal axis of the connector arm and the second sleeve and the second locking mechanism are configured to slidingly engage the second lower pair of dovetail grooves and the second upper pair of dovetail grooves, respectively, of the connector arm in a second direction generally parallel to the longitudinal axis of the connector arm and opposite the first direction.

4. The transverse connector of claim 1, wherein first end region of each of the first and second inserts comprises a threaded region.

5. The transverse connector of claim 4, wherein each of the first and second locking mechanisms comprises a threaded through hole.

6. The transverse connector of claim 5, wherein the first and second locking mechanisms are configured to threadably engage the threaded region of the first and second inserts, respectively.

7. The transverse connector of claim 6, wherein rotating either of the first or second locking mechanisms in a first direction raises the corresponding insert into the aperture of the sleeve.

8. The transverse connector of claim 7, wherein rotating either of the first or second locking mechanisms in a second direction, opposite the first direction, lowers the corresponding insert out of the aperture of the sleeve.

9. The transverse connector of claim 1, wherein the second end region of each of the first and second inserts comprises two deflectable arms.

10. The transverse connector of claim 9, wherein the deflectable arms of each of the first and second inserts are configured to engage an elongate member of a spinal stabilization system.

11. A transverse connector for coupling between first and second elongate members of a spinal stabilization system, the transverse connector comprising:
a connector arm having a first end portion, a second end portion and a bridge member extending therebetween along a longitudinal axis, the first end portion having a first through hole extending from a top surface to a bottom surface and the second end portion having a second through hole extending from a top surface to a bottom surface, wherein the connector arm further includes a first upper pair of dovetail grooves extending along the top surface adjacent to the first through hole, a first lower pair of dovetail grooves extending along the bottom surface adjacent to the first through hole, a second upper pair of dovetail grooves extending along the top surface adjacent to the second through hole, and a second lower pair of dovetail grooves extending along the bottom surface adjacent to the second through hole;
a first coupling assembly proximate the first end portion of the connector arm, the first coupling assembly comprising:
a first sleeve having a top surface, a bottom surface, an aperture extending between the top surface and the bottom surface, and a pair of dovetail grooves extending along the top surface and configured to slidably engage the first pair of lower dovetail grooves of the connector arm in a direction generally parallel to the longitudinal axis of the connector arm;
a first insert having a first end region and a second end region, the first insert movably disposed within the aperture of the first sleeve; and
a first locking mechanism having a dovetail groove extending around a perimeter of a lower portion thereof and configured to slidably engage the first pair of upper dovetail grooves of the connector arm in a direction generally parallel to the longitudinal axis of the connector arm;
a second coupling assembly proximate the second end portion of the connector arm, the second coupling assembly comprising:
a second sleeve having a top surface, a bottom surface, an aperture extending between the top surface and the bottom surface, and a pair of dovetail grooves extending along the top surface and configured to slidably engage the second pair of lower dovetail grooves of the connector arm in a direction generally parallel to the longitudinal axis of the connector arm;
a second insert having a first end region and a second end region, the second insert movably disposed within the aperture of the second sleeve; and
a second locking mechanism having a dovetail groove extending around a perimeter of a lower portion thereof and configured to slidably engage the second pair of upper dovetail grooves of the connector arm in a direction generally parallel to the longitudinal axis of the connector arm.

12. The transverse connector of claim 11, wherein first end region of each of the first and second inserts comprises a threaded region and the second end region of each of the first and second inserts comprises two deflectable arms.

13. The transverse connector of claim 12, wherein the deflectable arms of each of the first and second inserts are configured to engage an elongate member of a spinal stabilization system.

14. The transverse connector of claim 12, wherein each of the first and second locking mechanisms comprises a through hole having a threaded region, the threaded region having a major diameter and a minor diameter, wherein the minor diameter decreases towards the lower portion of the locking mechanisms.

15. The transverse connector of claim 14, wherein the first and second locking mechanisms are configured to threadably engage the threaded region of the first and second inserts, respectively.

16. The transverse connector of claim 15, wherein rotating either of the first or second locking mechanisms in a first direction raises the corresponding insert into the aperture of the sleeve.

17. The transverse connector of claim 16, wherein rotating either of the first or second locking mechanisms in a second direction, opposite the first direction, lowers the corresponding insert out of the aperture of the sleeve.

18. A spinal stabilization system comprising:
a first elongate member;
a second elongate member;
a transverse connector extending between the first elongate member and the second elongate member, the transverse connector comprising:
a connector arm having a first end portion, a second end portion and a bridge member extending therebetween, the first end portion having a first through hole extending from a top surface to a bottom surface and the second end portion having a second through hole extending from a top surface to a bottom surface, wherein the connector arm further includes a first upper pair of dovetail grooves extending along the top surface adjacent to the first through hole, a first lower pair of dovetail grooves extending along the bottom surface adjacent to the first through hole, a second upper pair of dovetail grooves extending along the top surface adjacent to the second through hole, a second lower pair of dovetail grooves extending along the bottom surface adjacent to the second through hole;
a first coupling assembly proximate the first end portion of the connector arm, the first coupling assembly comprising:

a first sleeve having a top surface, a bottom surface, an aperture extending between the top surface and the bottom surface, and a pair of dovetail grooves extending along the top surface slidably engaged with the first lower pair of dovetail grooves of the connector arm;

a first insert extending through the first through hole, the first insert having a first threaded end region and a second end region coupled to the first elongate member; and a first locking mechanism threadably engaged with the first threaded end region of the first insert, the first locking mechanism having a dovetail groove extending around a perimeter of a lower portion thereof engaged with the first upper pair of dovetail grooves of the connector arm;

a second coupling assembly proximate the second end portion of the connector arm, the second coupling assembly comprising:

a second sleeve having a top surface, a bottom surface, an aperture extending between the top surface and the bottom surface, and a pair of dovetail grooves extending along the top surface slidably engaged with the second lower pair of dovetail grooves of the connector arm;

a second insert extending through the second through hole, the second insert having a first threaded end region and a second end region coupled to the second elongate member; and a second locking mechanism threadably engaged with the first threaded end region of the second insert, the second locking mechanism having a dovetail groove extending around a perimeter of a lower portion thereof engaged with the second upper pair of dovetail grooves of the connector arm.

19. The spinal stabilization system of claim 18, wherein the connector arm has a longitudinal axis and the first sleeve and the first locking mechanism are configured to slidingly engage the first lower pair of dovetail grooves and the first upper pair of dovetail grooves, respectively, of the connector arm in a first direction generally parallel to the longitudinal axis of the connector arm and the second sleeve and the second locking mechanism are configured to slidingly engage the second lower pair of dovetail grooves and the second upper pair of dovetail grooves, respectively, of the connector arm in a second direction generally parallel to the longitudinal axis of the connector arm and opposite the first direction.

20. The spinal stabilization system of claim 18, wherein the first insert is rotatable in the first through hole through an angle of less than 360° and the second insert is rotatable in the second through hole through an angle of less than 360°.

* * * * *